(12) United States Patent
Moon et al.

(10) Patent No.: US 10,966,969 B2
(45) Date of Patent: Apr. 6, 2021

(54) THERAPEUTIC AGENT FOR LIVER DISEASES

(71) Applicant: APTABIO THERAPEUTICS INC., Yongin-si (KR)

(72) Inventors: Sung Hwan Moon, Suwon-si (KR); Soo Jin Lee, Suwon-si (KR); Sung Chan Lee, Suwon-si (KR); Yun Soo Bae, Goyang-sI (KR)

(73) Assignee: APTABIO THERAPEUTICS INC., Yongin-si (KR)

( * ) Notice: Subject to any disclaimer, the term of this patent is extended or adjusted under 35 U.S.C. 154(b) by 76 days.

(21) Appl. No.: 16/481,307

(22) PCT Filed: Sep. 14, 2018

(86) PCT No.: PCT/KR2018/010857
§ 371 (c)(1),
(2) Date: Jul. 26, 2019

(87) PCT Pub. No.: WO2019/088444
PCT Pub. Date: May 9, 2019

(65) Prior Publication Data
US 2020/0390752 A1    Dec. 17, 2020

(30) Foreign Application Priority Data
Nov. 1, 2017 (KR) .................. 10-2017-0144911

(51) Int. Cl.
*A61K 31/4439* (2006.01)
*A61P 1/16* (2006.01)

(52) U.S. Cl.
CPC ............ *A61K 31/4439* (2013.01); *A61P 1/16* (2018.01)

(58) Field of Classification Search
CPC .................. A61K 31/4439; A61P 1/16
See application file for complete search history.

(56) References Cited

U.S. PATENT DOCUMENTS

| 2010/0137582 A1 | 6/2010 | Endo et al. |
| 2012/0220550 A1* | 8/2012 | Bae ............ C07D 405/14 514/63 |

(Continued)

FOREIGN PATENT DOCUMENTS

| CN | 104288149 B | 2/2017 |
| ES | 2550820 T3 | 11/2015 |

(Continued)

OTHER PUBLICATIONS

Jin Choo Cha et al., "APX-115, a first-in-class pan-NADPH oxidase (Nox) inhibitor, protects db/db mice from renal injury" Laboratory Investigation, vol. 97, No. 4, Feb. 6, 2017 (Feb. 6, 2017), pp. 419-431, XP055674234, The United States and Canadian Academy of Pathology, Inc.

(Continued)

*Primary Examiner* — Valerie Rodriguez-Garcia
(74) *Attorney, Agent, or Firm* — Joseph V. Saphia; Haug Partners LLP

(57) ABSTRACT

Disclosed is a pharmaceutical composition for preventing or treating a fatty liver disease containing, as an active ingredient, a pyrazole-based compound or a pharmaceutically acceptable salt thereof. 3-phenyl-4-alkyl-1-(pyridin-2-yl)-1H-pyrazol-5-ol or a pharmaceutically acceptable salt thereof is capable of effectively inhibiting fatty liver, hepatic inflammation and hepatic fibrosis, and is useful for preventing or treating NAFLD, in particular, NASH.

11 Claims, 9 Drawing Sheets

MCD Rat model-Liver tissue lipid Oil red O staining

| Negative control | Vehicle control | Compound 1 |

(56) References Cited

U.S. PATENT DOCUMENTS

| | | | |
|---|---|---|---|
| 2014/0066404 A1 | 3/2014 | Bae et al. | |
| 2014/0088152 A1* | 3/2014 | Bae | A61K 31/506 514/341 |
| 2014/0128418 A1 | 5/2014 | Bae et al. | |
| 2015/0218125 A1* | 8/2015 | Bae | C07D 405/14 514/275 |

FOREIGN PATENT DOCUMENTS

| | | |
|---|---|---|
| JP | 2007-210978 | 8/2007 |
| JP | 2013-249256 | 12/2013 |
| KR | 10-2009-0102145 | 9/2009 |
| KR | 10-2012-0098489 | 9/2012 |
| KR | 10-1840702 | 3/2018 |
| RU | 2600983 C2 | 10/2016 |
| WO | WO 2014/074628 A1 | 5/2014 |
| WO | WO 2017/155053 A1 | 9/2017 |

OTHER PUBLICATIONS

Apr. 1, 2017 (Apr. 1, 2017), pp. 1-7, XP055675260, Retrieved from the Internet: URL:https://static-content.springer.com/esm/art%3A10.1038%2Flabinvest.2017.2/MediaObjects/41374_2017_BFlabinvest20172_MOESM6_ESM.pdf [retrieved on Mar. 10, 2020].
Search Report issued in the corresponding European Patent Application No. 18871904.1 dated Mar. 19, 2020.
Office Action issued in the corresponding Russian Patent Application No. 2019123290 dated Feb. 11, 2020 and its English Translation.
Christopher P. Day & Oliver F.W. James (1998) "Steatohepatitis: A Tale of Two "Hits"?". Gastroenterology, vol. 114, No. 4, pp. 842-845.
Cha, J.J. et al., "APX-115, a first-in-class pan-NADPH oxidase (Nox) inhibitor protects db/db mice from renal injury," Laboratory Investigation, 2017, vol. 97, pp. 419-431.
Joo, J.H. et al., "A novel pyrazole derivative protects from ovariectomy-induced osteoporosis through the inhibition of NADPH oxidase," Scientific Reports, 2016, 6:22389, pp. 1-14, DOI: 10. 1038/srep22389.
Yuya Seko, "The Relationship Between Type 2 Diabetes Mellitus and Non-alcoholic Fatty Liver Disease," 2017, vol. 126(10), pp. 707-715.
Cohen, J.C. et al., "Human Fatty Liver Disease: Old Questions and New Insights", Science, Jun. 24, 2011, 332(6037): 1519-1523.
Szczepaniak L.S. et al., "Magnetic resonance spectroscopy to measure hepatic triglyceride content: prevalence of hepatic steatosis in the general population", Am J Physiol Endocrinol Metab 2005; 288: E462-E468.
Birkenfeld A.L., "Nonalcoholic Fatty Liver Disease, Hepatic Insulin Resistance, and Type 2 Diabetes", Hepatology 2014;59:713-723.
Musso G. et al., "Recent insights into hepatic lipid metabolism in non-alcoholic fatty liver disease (NAFLD)", Progress in Lipid Research 48, 2009; 48, 1-26.
Guilherme A. et al., "Adipocyte dysfunctions linking obesity to insulin resistance and type 2 diabetes", Nat Rev Mol Cell Biol 2008;9:367-377.
Day CP, James OF. Gastroenterology 1998;114:842-845.
Matteoni, C.A. et al., "Nonalcoholic Fatty Liver Disease: A Spectrum of Clinical and Pathological Severity", Gastroenterology 1999; 116: 1413-1419.
Single Topic Conference 2002 Neuschwander-Tetri, B.A., et al, 2003, Hepatology, 37: 1202-1219.
International Search Report and Written Opinion dated Dec. 20, 2018 in corresponding International Application No. PCT/KR2018/010857.
Office Action issued in corresponding Australian Patent Application No. 2018358496 dated Nov. 27, 2019.

* cited by examiner

MCD Rat model-Liver tissue TNF-$\alpha$ staining

[Fig. 3a]

MCD Rat model-Liver tissue TGF-$\beta$ staining

[Fig. 3b]

MCD Rat model-Liver tissue Inflammation H&E staining

[Fig. 3c]

MCD Rat model-Liver tissue lipid Oil red O staining

TGF-β staining in Liver

[Fig. 5b]

Type IV Collagen staining in Liver

THERAPEUTIC AGENT FOR LIVER DISEASES

CROSS-REFERENCE TO RELATED APPLICATIONS

This application is the National Stage entry under 35 U.S.C. § 371 of International Application No. PCT/KR2018/010857 filed on Sep. 14, 2018, published on May 9, 2019 under Publication Number WO 2019/088444, which claims the benefit of priority under 35 U.S.C. § 119 of Korean Patent Application Number 10-2017-0144911 filed Nov. 1, 2017 the entireties of which are herein incorporated by reference.

TECHNICAL FIELD

The present invention relates to a therapeutic agent for liver diseases containing, as an active ingredient, a pyrazole-based compound or a pharmaceutically acceptable salt thereof.

BACKGROUND ART

Non-alcoholic fatty liver diseases (NAFLDs), which are the most common chronic liver diseases, are known to be closely associated with Type 2 diabetes, obesity and metabolic syndrome [Cohen J C, Horton J D, Hobbs H H. Science 2011; 332:1519-23.].

Non-alcoholic fatty liver diseases refer to fatty liver conditions in which excess neutral fat is deposited in the liver and, in a broad sense, include simple steatosis, non-alcoholic steatohepatitis (NASH) and cirrhosis [Cohen J C, Horton J D, Hobbs H H. Science 2011; 332:1519-23.].

In addition to obesity, diabetes and dyslipidemia, non-alcoholic fatty liver diseases are considered to be important factors of metabolic syndrome and most metabolic syndrome patients suffer non-alcoholic fatty liver diseases [Szczepaniak L S, Nurenberg P, Leonard D, Browning J D, Reingold J S, Grundy S, Hobbs H H, Dobbins R L. Am J Physiol Endocrinol Metab 2005; 288: E462-8]. In general, non-alcoholic fatty liver diseases occur when neutral fat synthesis exceeds neutral fat digestion in the liver, for example, when absorption of free fatty acid in the liver is increased or biosynthesis of neutral fat is increased by carbohydrate metabolism [Birkenfeld A L, Shulman G I. Hepatology 2014; 59:713-23.] Free fatty acid, which is an ingredient for neutral fat synthesis occurring in the liver, is incorporated into the liver by dietary or in vivo biosynthesis and is released from adipose tissues [Musso G, Gambino R, Cassader M. Prog Lipid Res 2009; 48:1-261.].

Chronic inflammation in adipocytes occurring due to prolonged hypernutrition may cause facilitated lipolysis, increased fatty acid and neutral fat in blood, and infiltration of macrophages in adipocytes, which results in secretion of TNF-α which is a typical inflammatory cytokine. This leads to increased incorporation of fatty acid in skeletal muscle, resulting in an increase in the amount of fat accumulated in the skeletal muscles and insulin resistance in the muscles [Guilherme A, Virbasius J V, Puri V, Czech M P. Nat Rev Mol Cell Biol 2008; 9:367-77].

In general, the causes of nonalcoholic fatty liver diseases have been explained based on two hit hypothesis.

The first hit is deposition of neutral fats in the liver due to insulin resistance and increased free fatty acid. The second hit is that oxidative stress causes peroxidation of fat and thus changes in necrotic inflammation, which is found to induce histological changes known as "non-alcoholic steatohepatitis" [Day C P, James O F. Gastroenterology 1998; 114:842-5].

Representative mechanisms in which lipid metabolites show hepatocyte injury and toxicity include endoplasmic reticulum stress and oxidative stress. When proteins that fail to change their structures suitably (unfolded proteins) are accumulated in the endoplasmic reticulum, unfolded protein response (UPR) is induced, activating IRE1, ATF6, and PERK. These reactions have been shown to activate NF-κB, c-Jun N-terminal kinase, and oxidative stress pathways, which contribute to the progression from simple steatosis to steatohepatitis [Birkenfeld A L, Shulman G I. Hepatology 2014; 59:713-23].

Meanwhile, there is no research disclosing that the pyrazole-based compound of the present invention has effects of preventing and treating fatty liver diseases.

Prior Art

Patent Document (Patent Document 1) Korean Patent No. 10-1280160
(Patent Document 2) Korean Patent No. 10-1633957

Non-Patent Document (Non-patent Document 1) Cohen J C, Horton J D, Hobbs H H. Science 2011; 332:1519-23.
(Non-patent Document 2) Szczepaniak L S, Nurenberg P, Leonard D, Browning J D, Reingold J S, Grundy S, Hobbs H H, Dobbins R L. Am J Physiol Endocrinol Metab 2005; 288: E462-8.
(Non-patent Document 3) Birkenfeld A L, Shulman G I. Hepatology 2014; 59:713-23.
(Non-patent Document 4) Musso G, Gambino R, Cassader M. Prog Lipid Res 2009; 48:1-26.
(Non-patent Document 5) Guilherme A, Virbasius J V, Puri V, Czech M P. Nat Rev Mol Cell Biol 2008; 9:367-77.
(Non-patent Document 6) Day C P, James O F. Gastroenterology 1998; 114:842-5.

DISCLOSURE OF INVENTION

Technical Problem

In view of the above problems, the present inventors completed the present invention based on the finding that, in a variety of fatty liver disease animal models, fatty liver, hepatic inflammation and hepatic fibrosis, which are the main pathologies of fatty liver diseases, can be effectively cured by treatment with the pyrazole-based compound of the present invention.

During continuous research on effective therapeutic agents for treating liver diseases, the present inventors found that a compound having a core structure of 3-phenyl-4-alkyl-1-(pyridin-2-yl)-1H-pyrazol-5-ol inhibits inflammatory cytokine derived from the fatty liver and thereby has an effect of inhibiting hepatic inflammation and hepatic fibrosis. The present invention has been completed based on these findings.

Therefore, it is an object of the present invention to provide a pharmaceutical composition for preventing, alleviating or treating liver diseases containing, as an active ingredient, a pyrazole-based compound having a core structure of 3-phenyl-4-alkyl-1-(pyridin-2-yl)-1H-pyrazol-5-ol or a pharmaceutically acceptable salt thereof.

Solution to Problem

In accordance with the present invention, the above and other objects can be accomplished by the provision of a pharmaceutical composition for preventing, alleviating or treating liver diseases containing, as an active ingredient, at least one compound selected from a pyrazole-based compound represented by the following Formula 1 and a pharmaceutically acceptable salt thereof:

[Formula 1]

wherein R is a C1-C10 linear or branched alkyl group.

In accordance with another aspect of the present invention, provided is a method for preventing, alleviating or treating a liver disease of a liver disease patient including administering an effective amount of at least one compound selected from the pyrazole-based compound represented by Formula 1 and a pharmaceutically acceptable salt thereof, to a subject in need thereof.

In accordance with another aspect of the present invention, provided is at least one compound selected from the pyrazole-based compound represented by Formula 1 and a pharmaceutically acceptable salt thereof for preventing, alleviating or treating a liver disease of a liver disease patient.

In accordance with another aspect of the present invention, provided is use of at least one compound selected from the pyrazole-based compound represented by Formula 1 and a pharmaceutically acceptable salt thereof for preparing an agent for preventing, alleviating or treating a liver disease of a liver disease patient.

Advantageous Effects of Invention

The pyrazole-based compound or a pharmaceutically acceptable salt thereof according to the present invention is capable of effectively inhibiting fatty liver, hepatic inflammation and hepatic fibrosis, and is useful for prevention or treatment of NAFLD, in particular, NASH.

The term "fatty liver disease" used herein broadly refer to diseases in which fat is accumulated in liver cells, causing hepatopathy, and includes alcoholic hepatopathy and non-alcoholic fatty liver (NAFLD or NASH).

BRIEF DESCRIPTION OF DRAWINGS

The above and other objects, features and other advantages of the present invention will be more clearly understood from the following detailed description taken in conjunction with the accompanying drawings, in which.

BEST MODE FOR CARRYING OUT THE INVENTION

Reference will now be made in detail to the preferred embodiments of the present invention, examples of which are illustrated in the accompanying drawings. Wherever possible, the same reference numbers will be used throughout the drawings to refer to the same or like parts.

In one embodiment of the present invention, the liver disease may be a fatty liver disease, the fatty liver disease may be non-alcoholic fatty liver or simple fatty liver, and the composition according to one embodiment of the present invention has effects of inhibiting accumulation of fat in the liver, suppressing inflammatory cytokine derived from the fatty liver and thereby inhibiting hepatic inflammation and hepatic fibrosis.

It should be understood that, in the specification, when the range is referred to regarding a parameter, the parameter encompasses all figures including end points disclosed within the range. For example, the range of "5 to 10" includes figures of 5, 6, 7, 8, 9, and 10, as well as arbitrary sub-ranges such as ranges of 6 to 10, 7 to 10, 6 to 9, and 7 to 9, and any figures, such as 5.5, 6.5, 7.5, 5.5 to 8.5 and 6.5 to 9, between appropriate integers that fall within the range. In addition, for example, the range of "10% to 30%" encompasses all integers that include values such as 10%, 11%, 12% and 13%, as well as 30%, and any sub-ranges of 10% to 15%, 12% to 18%, or 20% to 30%, as well as any figures, such as 10.5%, 15.5% and 25.5%, between appropriate integers that fall within the range.

Hereinafter, the present invention will be described in detail.

The present invention relates to a pharmaceutical composition for preventing, alleviating or treating liver diseases containing, as an active ingredient, at least one compound selected from a pyrazole-based compound represented by the following Formula 1 and a pharmaceutically acceptable salt thereof:

[Formula 1]

wherein R is a C1-C10 linear or branched alkyl group.

The term "fatty liver disease" as used herein broadly refers to a disease in which fat is accumulated in liver cells, causing hepatopathy, and includes alcoholic hepatopathy and non-alcoholic fatty liver (NAFLD or NASH). Non-alcoholic steatohepatitis (NAFLD or NASH) is classified into four types depending on progression degree. Type 1 is simple fatty liver, type 2 is fatty hepatitis, type 3 is fatty liver necrosis, and type 4 includes hepatic necrosis involving fibrosis. Based on the long-term prognostic review, types 3 and 4 that have significantly higher progression to cirrhosis or liver-related mortality are defined as NASH stages. [Matteoni, C. A., et al 1999, Gastroenterology, 116: 1413-1419]. At Single Topic Conference 2002 of the American Association for the Study of Liver Diseases, stages 3 and 4 of NAFLD are considered as NASH in view of steatosis, lobular inflammation and hepatocellular ballooning as the conditions of NASH [Single Topic Conference 2002, Neuschwander-Tetri, B. A., et al, 2003, Hepatology, 37: 1202-1219].

The fatty liver disease, to which the prophylactic or therapeutic agent according to the present invention is applied, is preferably non-alcoholic fatty liver (NAFLD), particularly preferably, simple fatty liver, or non-alcoholic steatohepatitis (NASH).

The pharmaceutically acceptable salt of the pyrazole-based compound contained in the pharmaceutical composition of the present invention means a salt commonly used in the pharmaceutical industry and examples thereof include: inorganic acid salts prepared with hydrochloric acid, nitric acid, phosphoric acid, bromic acid, iodic acid, perchloric acid, sulfuric acid and the like; organic acid salts prepared with acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid and the like; sulfonic acid salts prepared with methanesulfonic acid, ethanesulfonic acid, benzenesulfonic acid, p-toluenesulfonic acid, naphthalenesulfonic acid and the like; and the like, and the type of salt according to the present invention is not limited thereto. Preferably, the pharmaceutically acceptable salt is hydrochloride.

Specifically, examples of the pyrazole-based compound represented by Formula 1 contained in the pharmaceutical composition of the present invention are given below:
3-phenyl-4-methyl-1-(pyridin-2-yl)-1H-pyrazol-5-ol or hydrochloride thereof;
3-phenyl-4-ethyl-1-(pyridin-2-yl)-1H-pyrazol-5-ol or hydrochloride thereof;
3-phenyl-4-normalpropyl-1-(pyridin-2-yl)-1H-pyrazol-5-ol or hydrochloride thereof;
3-phenyl-4-isopropyl-1-(pyridin-2-yl)-1H-pyrazol-5-ol or hydrochloride thereof;
3-phenyl-4-normalbutyl-1-(pyridin-2-yl)-1H-pyrazol-5-ol or hydrochloride thereof;
3-phenyl-4-tert-butyl-1-(pyridin-2-yl)-1H-pyrazol-5-ol or hydrochloride thereof;
3-phenyl-4-normalpentyl-1-(pyridin-2-yl)-1H-pyrazol-5-ol or hydrochloride thereof; and
3-phenyl-4-normalhexyl-1-(pyridin-2-yl)-1H-pyrazol-5-ol or hydrochloride thereof.

More specifically, the pyrazole-based compound represented by Formula 1 contained in the pharmaceutical composition of the present invention may be 3-phenyl-4-normalpropyl-1-(pyridin-2-yl)-1H-pyrazol-5-ol or hydrochloride thereof.

The composition of the present invention may further include a pharmaceutically acceptable additive such as a diluent, a binder, a disintegrant, a lubricant, a pH adjuster, an antioxidant or a solubilizing agent so long as it does not impair the effects of the present invention.

The diluent may be sugar, starch, microcrystalline cellulose, lactose (lactose hydrate), glucose, di-mannitol, alginate, alkaline earth metal salts, clay, polyethylene glycol, anhydrous calcium hydrogen phosphate, a mixture thereof or the like, and the binder may be starch, microcrystalline cellulose, highly dispersible silica, mannitol, di-mannitol, sucrose, lactose hydrate, polyethylene glycol, polyvinyl pyrrolidone (povidone), polyvinyl pyrrolidone copolymers (copovidone), hypromellose, hydroxypropyl cellulose, natural gum, synthetic gum, gelatin, a mixture thereof or the like.

The disintegrant may be: starch or modified starch such as sodium starch glycolate, corn starch, potato starch or pregelatinized starch; clay such as bentonite, montmorillonite or Veegum; cellulose such as microcrystalline cellulose, hydroxypropyl cellulose or carboxy methylcellulose; alginate such as sodium alginate or alginic acid; crosslinked cellulose such as croscarmellose sodium; gum such as guar gum or xanthan gum; a crosslinked polymer such as crosslinked polyvinyl pyrrolidone (crospovidone); an effervescent agent such as sodium bicarbonate or citric acid; or a mixture thereof.

The lubricant may be talc, stearic acid, magnesium stearate, calcium stearate, sodium lauryl sulfate, a hydrogenated vegetable oil, sodium benzoate, sodium stearyl fumarate, glyceryl behenate, glyceryl monooleate, glyceryl monostearate, glyceryl palmitostearate, colloidal silicon dioxide, a mixture thereof or the like.

The pH adjuster may be an acidic pH adjuster such as acetic acid, adipic acid, ascorbic acid, sodium ascorbate, sodium etherate, malic acid, succinic acid, tartaric acid, fumaric acid or citric acid, or a basic pH adjuster such as precipitated calcium carbonate, ammonia water, meglumine, sodium carbonate, magnesium oxide, magnesium carbonate, sodium citrate, tribasic calcium phosphate or the like.

The antioxidant may be dibutyl hydroxytoluene, butylated hydroxyanisole, tocopheryl acetate, tocopherol, propyl gallate, sodium hydrogen sulfite, sodium pyrosulfite or the like. In the early release compartment of the present invention, the solubilizing agent may be a polyoxyethylene sorbitan fatty acid ester such as sodium lauryl sulfate or polysorbate, sodium docusate, a poloxamer or the like.

In addition, in order to prepare a sustained release formulation, an enteric polymer, a water-insoluble polymer, a hydrophobic compound and a hydrophilic polymer may be incorporated.

The enteric polymer refers to a polymer that is insoluble or stable under acidic conditions of less than pH 5, that is, a polymer that is dissolved or degraded at a certain pH of 5 or more and examples thereof include: enteric cellulose derivatives such as hypromellose acetate succinate, hypromellose phthalate (hydroxypropyl methylcellulose phthalate), hydroxymethyl ethylcellulose phthalate, cellulose acetate phthalate, cellulose acetate succinate, cellulose acetate maleate, cellulose benzoate phthalate, cellulose propionate phthalate, methylcellulose phthalate, carboxymethyl ethylcellulose, ethyl hydroxyethyl cellulose phthalate, and methyl hydroxyethyl cellulose; enteric acrylic acid-based copolymers such as styrene-acrylic acid copolymers, methyl acrylate-acrylic acid copolymers, methyl acrylate-methacrylic acid copolymers (for example, Acryl-EZE®), butyl acrylate-styrene-acrylic acid copolymers, and methyl acrylate-methacrylic acid-octyl acrylate copolymers; enteric polymethacrylate copolymers such as poly(methacrylic acid methyl methacrylate) copolymers (for example, Eudragit L, Eudragit S, Evonik Industries AG, Germany), and poly (methacrylic acid ethyl acrylate) copolymers (for example, Eudragit L100-55); enteric maleic acid-based copolymers such as vinyl acetate-maleic anhydride copolymers, styrene-maleic anhydride copolymers, styrene-maleic acid monoester copolymers, vinylmethyl ether-maleic anhydride copolymers, ethylene-maleic anhydride copolymers, vinyl butyl ether-maleic anhydride copolymers, acrylonitrile-methyl acrylate·maleic anhydride copolymers, and butyl acrylate-styrene-maleic anhydride copolymers; and enteric polyvinyl derivatives such as polyvinyl alcohol phthalate, polyvinyl acetate phthalate, polyvinyl butylate phthalate and polyvinyl acetate acetal phthalate.

The water-insoluble polymer refers to a pharmaceutically acceptable polymer for controlling the release of drugs, which is not dissolved in water. Examples of the water-insoluble polymer include polyvinyl acetate (for example, Kollicoat SR30D), water-insoluble polymethacrylate copolymers [for example, poly(ethylacrylate-methyl methacrylate) copolymers (for example, Eudragit NE30D, poly(ethylacrylate-methyl methacrylate-trimethylaminoethylmethacrylate) copolymers (for example, Eudragit RSPO) or the like], ethyl cellulose, cellulose ester, cellulose ether, cellulose acylate, cellulose diacylate, cellulose triacylate, cellulose acetate, cellulose diacetate, cellulose triacetate and the like.

The hydrophobic compound refers to a pharmaceutically acceptable water-insoluble substance for controlling the release of drugs. Examples of the hydrophobic compound include: fatty acid and fatty acid esters such as glyceryl palmitostearate, glyceryl stearate, glyceryl behenate, cetyl palmitate, glyceryl monooleate and stearic acid; fatty acid alcohols such as cetostearyl alcohol, cetyl alcohol and stearyl alcohol; waxes such as Carnauba wax, beeswax and microcrystalline wax; and inorganic substances such as talc, precipitated calcium carbonate, calcium monohydrogen phosphate, zinc oxide, titanium oxide, kaolin, bentonite, montmorillonite and Veegum.

The hydrophilic polymer refers to a pharmaceutically acceptable water-soluble polymer for controlling the release of drugs. Examples of the hydrophilic polymer include: sugars such as dextrin, polydextrin, dextran, pectin and pectin derivatives, alginate, polygalacturonic acid, xylan, arabinoxylan, arabinogalactan, starch, hydroxypropyl starch, amylose and amylopectin; cellulose derivatives such as hypromellose, hydroxypropyl cellulose, hydroxymethyl cellulose, hydroxyethyl cellulose, methylcellulose and sodium carboxymethyl cellulose; gums such as guar gum, locust bean gum, tragacanth, carrageenan, acacia gum, gum arabic, gellan gum and xanthan gum; proteins such as gelatin, casein and zein; polyvinyl derivatives such as polyvinyl alcohol, polyvinyl pyrrolidone, and polyvinylacetal diethylaminoacetate; hydrophilic polymethacrylate copolymers such as poly(butyl methacrylate-(2-dimethylaminoethyl)methacrylate-methyl methacrylate) copolymer (for example, Eudragit E100, Evonik Industries AG, Germany), and poly(ethyl acrylate-methyl methacrylate-triethylaminoethyl-methacrylate chloride) copolymers (for example, Eudragit RL, RS, Evonik Industries AG, Germany); polyethylene derivatives such as polyethylene glycol and polyethylene oxide; carbomers and the like.

Furthermore, the formulation of the present invention can be prepared using a variety of pharmaceutically acceptable additives selected from coloring and flavoring agents.

The scope of additive is not limited by the mentioned additives and the preparation can be carried out by using the selected additive in an ordinary range of dose.

The pharmaceutical composition according to the present invention can be prepared in the form of an oral formulation such as a powder, a granule, a tablet, a pill, a capsule, a suspension, an emulsion, a syrup or an aerosol, or an external preparation, a suppository or a sterile injection solution.

In an embodiment, the present invention provides a pharmaceutical composition for preventing, alleviating or treating liver diseases, containing the active ingredient in an amount of 0.01 to 90% by weight, based on the total weight of the pharmaceutical composition.

The dose of the pyrazole-based compound represented by Formula 1 or a pharmaceutically acceptable salt thereof in the agent for preventing or treating fatty liver diseases according to the present invention may be suitably changed depending on age, body weight and symptoms of patients, administration routes and the like. For example, a daily dose on an adult (60 kg) basis may be about 1 mg to about 1,000 mg, preferably about 10 mg to about 750 mg, for oral administration, and may be about 0.3 mg to about 200 mg for injection administration, and may be administered only once or portionwise several times a day.

Another embodiment of the present invention provides an agent for preventing or treating simple steatosis containing, as an active ingredient, at least one selected from 3-phenyl-4-normalpropyl-1-(pyridin-2-yl)-1H-pyrazol-5-ol and a pharmaceutically acceptable salt thereof.

Another embodiment of the present invention provides a therapeutic or prophylactic agent for non-alcoholic steatohepatitis containing, as an active ingredient, at least one selected from 3-phenyl-4-normalpropyl-1-(pyridin-2-yl)-1H-pyrazol-5-ol and a pharmaceutically acceptable salt thereof.

Another embodiment of the present invention provides a therapeutic or prophylactic agent for cirrhosis containing, as an active ingredient, at least one selected from 3-phenyl-4-normalpropyl-1-(pyridin-2-yl)-1H-pyrazol-5-ol and a pharmaceutically acceptable salt thereof.

The term "administration" used herein means that the composition according to the present invention for preventing or treating a fatty liver disease is injected into a patient by any suitable method. The administration route of the composition according to the present invention for preventing or treating a fatty liver disease may be any general route enabling the composition to reach the target tissue. Examples of the administration route include, but are not limited to, oral, intraperitoneal, intravenous, intramuscular, subcutaneous, intradermal, intranasal, intrapulmonary, rectal, intracavitary, intraperitoneal and intrathecal administrations.

Mode for the Invention

Hereinafter, preferred examples will be given for better understanding of the present invention. However, these examples are provided only for better understanding of the present invention and should not be construed as limiting the scope of the present invention.

SYNTHESIS EXAMPLE

In the present Synthesis Example, a representative example of a method for synthesizing a pyrazole-based compound contained as an active ingredient in a pharmaceutical composition for treating liver diseases will be described.

Synthesis Example 1

Synthesis of 3-phenyl-4-n-propyl-1-(pyridin-2-yl)-1H-pyrazol-5-ol 2-propyl-3-oxo-3-phenylpropionic acid ethyl ester (2.52 g, 10.7 mmol) and 10 mL of ethanol were charged in a round bottom flask, and a solution of 2-hydrazinopyridine (1.29 g, 1.18 mmol) diluted in 3 mL of ethanol was then slowly added dropwise thereto at 0° C. The resulting mixture was refluxed under heating at 100° C. for 3 days. The solvent was removed by distillation under reduced pressure and the resulting solids were washed with hexane and ethyl acetate, and then dried under vacuum to obtain the target compound in a yield of 82%.

$^1$H NMR (300 MHz, CDCl$_3$) δ 12.50 (1H, s), 8.27-8.25 (1H, m), 8.01 (1H, d, J=8.5 Hz), 7.81 (1H, m), 7.69 (2H, m), 7.48-7.34 (3H, m), 7.12-7.10 (1H, m), 2.54 (2H, d, J=7.5 Hz), 1.64 (2H, m), 0.93 (3H, t, J=7.3 Hz); EIMS (70 eV) m/z (rel intensity) 279 (M+, 37), 250 (100).

Synthesis Example 2

Synthesis of 3-phenyl-4-n-propyl-1-(pyridin-2-yl)-1H-pyrazol-5-ol hydrochloride (compound 1)

The 3-phenyl-4-n-propyl-1-(pyridin-2-yl)-1H-pyrazol-5-ol (280 mg, 1.0 mmol) prepared in Synthesis Example 1 was dissolved in 4 mL of ethyl ether in a round bottom flask and a solution of 2M HCl in 0.55 mL of ethyl ether was slowly added dropwise thereto at 0° C. The resulting solids were filtered under reduced pressure from the reaction solution, the solvent was removed, and the residue was washed with hexane and ethyl acetate and dried under vacuum to obtain the target compound (270 mg, 0.85 mmol).

$^1$H NMR (300 MHz, CDCl$_3$) δ 8.44 (1H, d, J=4.2 Hz), 8.0-8.03 (2H, m), 7.66-7.64 (2H, m), 7.48-7.42 (3H, m), 7.34-7.30 (1H, m), 2.49 (2H, brs), 2.43 (2H, t, J=7.5 Hz), 1.48 (2H, m), 0.48 (3H, t, J=7.3 Hz).

EXAMPLE

In the present Example, pharmaceutical actions of the pyrazole-based derivative contained as an active ingredient in the pharmaceutical composition for treating liver diseases will be identified in detail.

Example 1

Activity of 3-phenyl-4-n-propyl-1-(pyridin-2-yl)-1H-pyrazol-5-ol hydrochloride on Inhibition of Fatty Liver [Test Using Fatty Liver Model Animal Induced by MCD (methionine/choline deficient) Diet]

As subject animals, 6-week-old male Sprague Dawley (SD) rats were purchased. All rats were kept under standard conditions. When the rats became 12 weeks old after being bred for about 6 weeks, test substances were administered to the rats. Test groups were set based on ALT level in blood collected at 5 weeks.

For 5 weeks after the rats became 12 weeks old, test substances were separately administered to a vehicle administration group and a 3-phenyl-4-n-propyl-1-(pyridin-2-yl)-1H-pyrazol-5-ol hydrochloride administration group.

A normal control group was used as a negative control.

Blood was collected one day before the start of the experiment (from the jugular vein), and blood samples were collected on the 3 weeks, 5 weeks, 7 weeks, 9 weeks and on the day of the autopsy (24 hours after the fasting, total six times). In addition, plasma of each blood sample collected on the 5 weeks, 7 weeks, 9 weeks and on the day of the autopsy were analyzed.

After completion of the test, the animals were anesthetized, liver tissues were taken out from respective animals and blood for inspection was collected. The liver tissues were weighed and imaged. The liver tissues were immobilized in 10% buffered neutral formalin. The immobilized tissues were cut to a predetermined thickness, subjected to a general tissue treatment process, embedded in paraffin and produced into tissue sections with a size of 4 to 5 µm, and the tissue sections were subjected to Hematoxylin & Eosin (H&E stain) as a general staining method and were histopatho-logically observed.

In addition to H&E staining, Oil red-O staining was conducted in order to observe lipids induced by formation of fatty liver, levels of produced lipids were measured and an effect of drug administration on reduction of lipids was predicted. The liver tissues were stained with an Oil red O working solution, to evaluate levels of produced lipids. Blood was collected and centrifuged at 3000 rpm at 4° C. for 10 min. The serum of the upper layer was taken and the level of alanine transaminase (ALT) was measured using an automatic blood biochemical analyzer (AU480, Beckman 30-18 Coulter, USA) and the results were analyzed.

A ratio of liver weight to body weight was measured and the amount of triglyceride in liver tissues was measured to expect effects of drug administration on reduction of relative liver weight and triglyceride. The liver tissues were ground with a homogenizer, chloroform and methanol (2:1) were added thereto, the resulting mixture was centrifuged at 3,000 rpm and at 4° C. for 10 minutes and the organic solvent layer containing lipids was separated. The organic solvent in the separated lipids layer was removed in the dryer at 50° C. for 12 hours. The lipid-only tubes were immersed in 100% EtOH, and then suspended in a lipid-free tube and then assayed with a kit reagent for measuring triglyceride (AM157S-K, Asan, Korea).

In order to observe immunohistochemical changes of liver tissues, thin sections were produced from the tissues immobilized in 10% buffered neutral formalin, were adhered to a coating slide, deparaffined and stained, and were then reacted with antibodies TNF-α (Tumor necrosis factor-α ab1793, Abcam), TGF-β (Transforming growth factor-β, ab66043, Abcam), α-SMA (α-smooth muscle actin, ab7817, Abcam) and IL-1β (Interleukin-1β, ab9722, Abcam) on respective slides. Results are analyzed.

Figure 1:
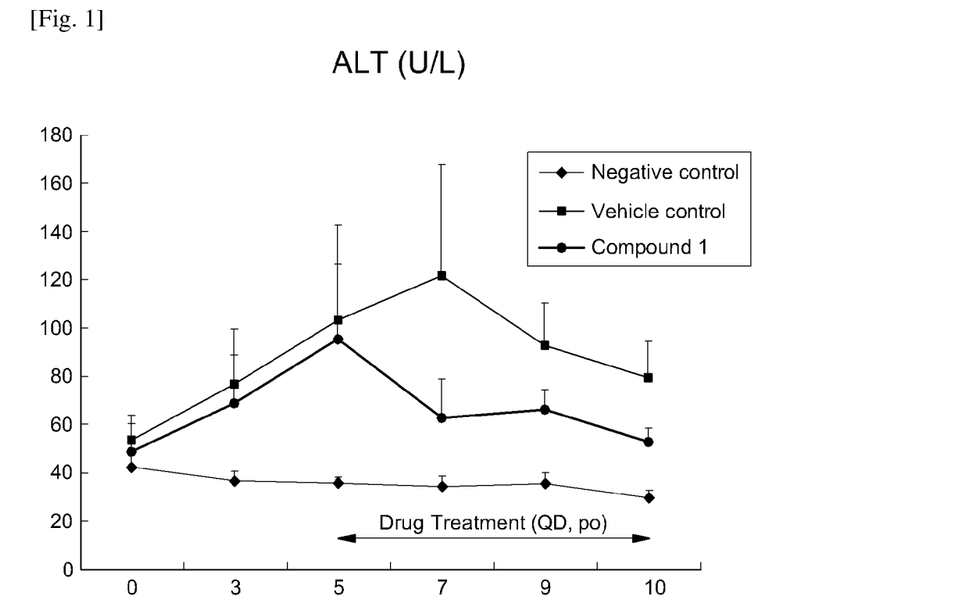
FIG. 1 is a graph showing a decrease of ALT in blood in a test using a fatty liver model animal induced by an MCD (methionine/choline deficient) diet.
Figure 2A:
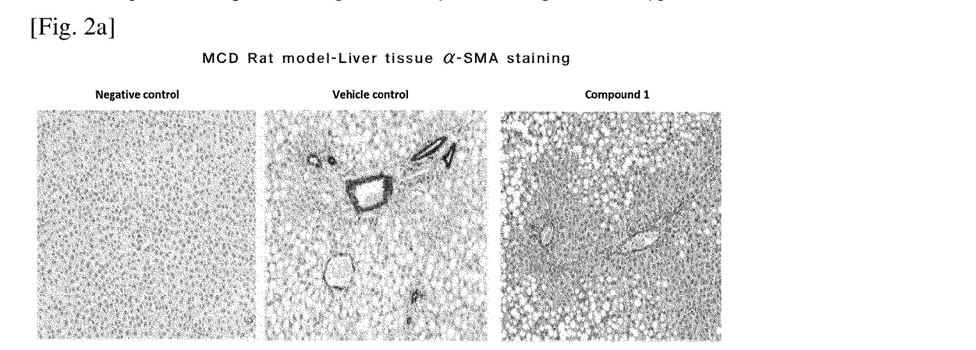
FIG. 2 is an image showing an effect of inhibition of inflammation in the liver tissues in a test using a fatty liver model animal induced by an MCD (methionine/choline deficient) diet.
Figure 2B:
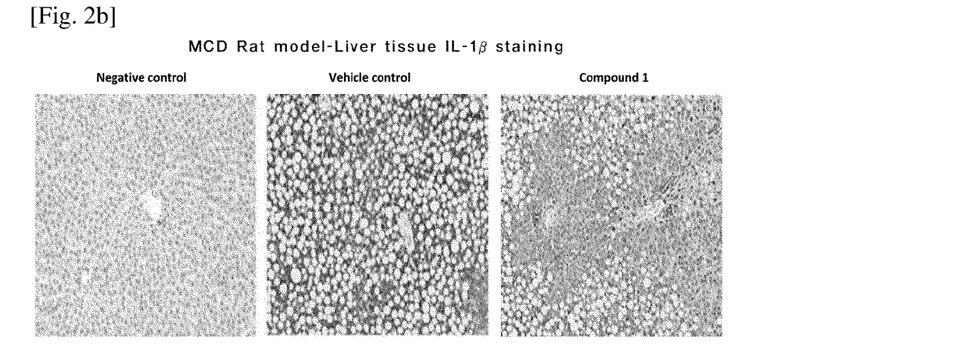
Figure 2C:
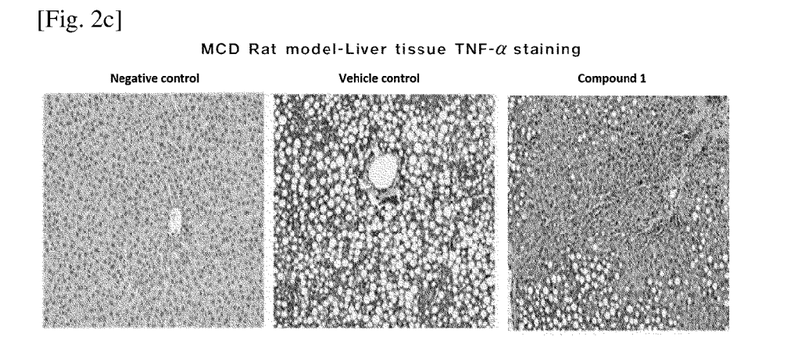
Figure 3A:
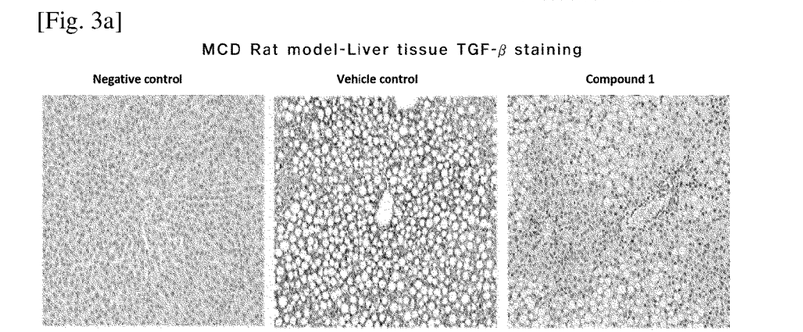
FIG. 3 is an image showing an effect of inhibition of fibrosis in the liver tissues in a test using a fatty liver model animal induced by an MCD (methionine/choline deficient) diet.
Figure 3B:
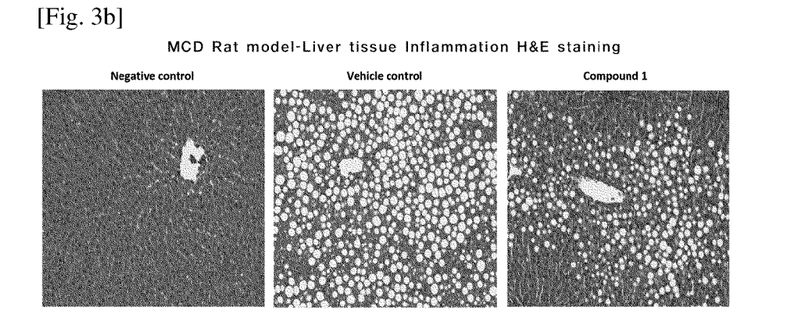
Figure 3C:
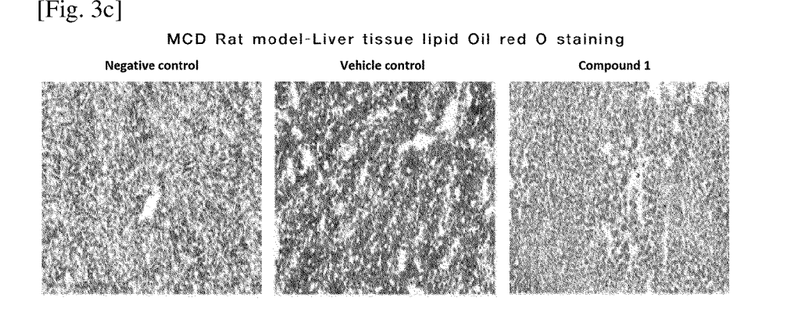
Figure 4A:
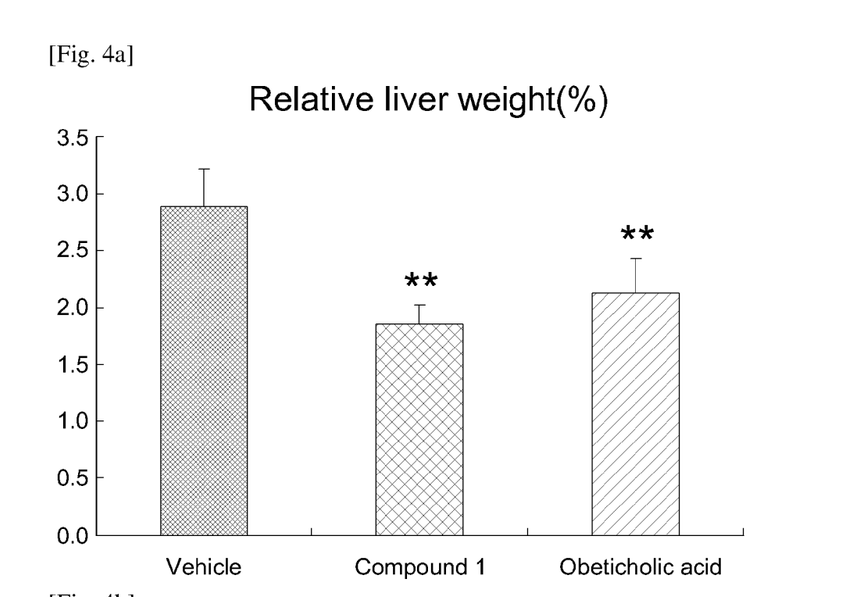
FIG. 4 shows effects of reduction of relative liver weight and levels of ALT, ALP and AST in blood in a test using a fatty liver model animal induced by a high fat diet.
Figure 4B:
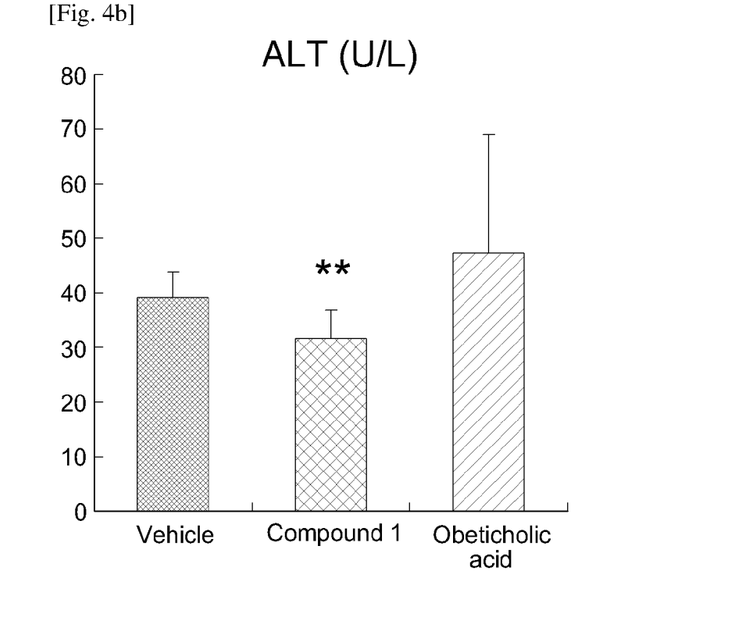
Figure 4C:
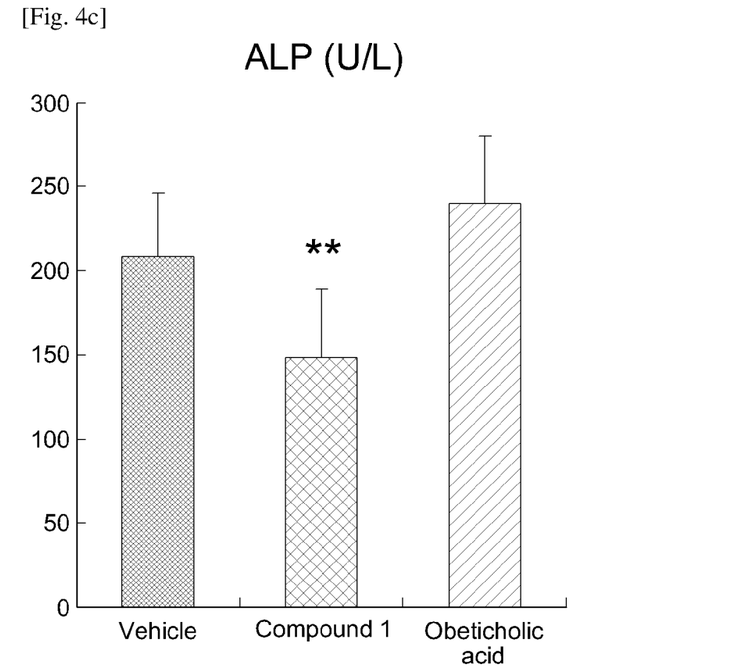
Figure 4D:
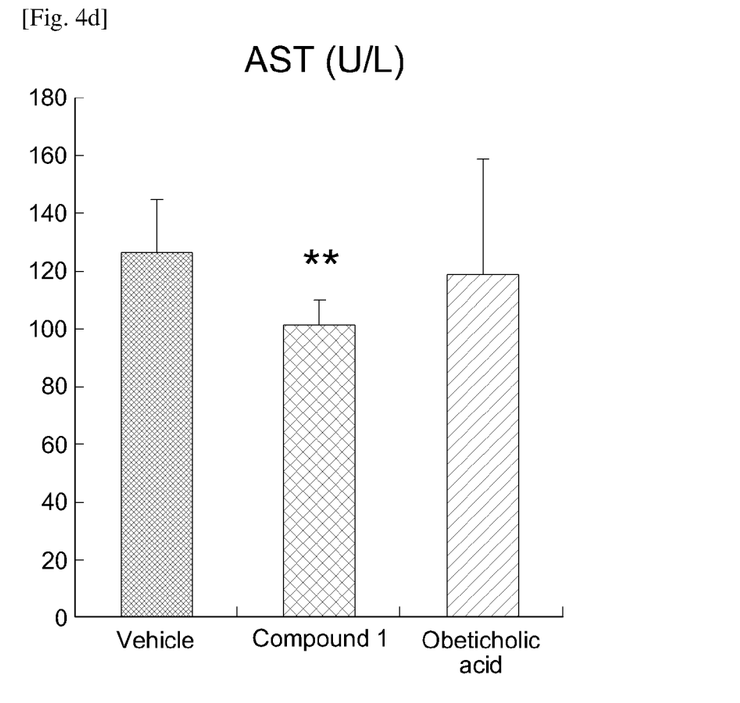

FIGS. 1, 2 and 3 are images showing that, in a test using a fatty liver model animal induced by an MCD (methionine/choline deficient) diet, a group, to which 3-phenyl-4-n-propyl-1-(pyridin-2-yl)-1H-pyrazol-5-ol hydrochloride is administered as a drug in a daily single dose of 60 mg/kg, has effects of reducing ALT level in blood, and inhibiting inflammation of liver tissues and inhibiting fibrosis of liver tissues. As shown in FIGS. 1, 2 and 3, in FIG. 1, the level of ALT in the blood is significantly reduced in the drug-administered group, as compared to the vehicle group, after administration of the drug. FIG. 2 shows staining results of α-SMA, IL-1β and TNF-α, as inflammation factors in liver tissues, which indicates that inflammation is considerably reduced in the drug-administered group, as compared to the vehicle group. FIG. 3 shows results of TGF-β, H&E staining, and Oil red O staining of liver tissues in order to identify liver tissue damage and hepatic fibrosis, which indicates that liver tissue damage and hepatic fibrosis are reduced in the drug-administered group, as compared to the vehicle group.

Example 2

Activity of 3-phenyl-4-normal-propyl-1-(pyridin-2-yl)-1H-pyrazol-5-ol hydrochloride on inhibition of fatty liver [Test using fatty liver model animal induced by high fat diet]

As subject animals, 6-week-old rats were purchased. All rats were kept under standard conditions. When the rats became 12 weeks old after being bred for about 6 weeks, test substances were administered to the rats. Test groups were set based on ALT level in blood collected at 5 weeks. For 5 weeks after the rats reached 12 weeks old, test substances were separately administered to a vehicle administration group, an obeticholic acid administration group as a positive control group, and a 3-phenyl-4-normalpropyl-1-(pyridin-2-yl)-1H-pyrazol-5-ol hydrochloride administration group.

Blood was collected one day before the start of the experiment (from jugular vein), and blood samples were collected on the 5 weeks, 8 weeks and on the day of the autopsy (24 hours after the fasting, total 4 times). In addition, plasma of each blood sample collected on the 5th week, 8th week and the day of the autopsy were analyzed.

After completion of the test, the animals were anesthetized, liver tissues were taken out from respective animals and blood for inspection was collected. The liver tissues were weighed and imaged. The liver tissues were immobilized in 10% buffered neutral formalin. The immobilized tissues were cut to a predetermined thickness, subjected to a general tissue treatment process, embedded in paraffin and produced into tissue sections with a size of 4 to 5 µm, and the tissue sections were subjected to Hematoxylin & Eosin (H&E stain) as a general staining method and were histopatho-logically observed.

In addition to H&E staining, Oil red-o staining was conducted in order to observe lipids induced by formation of fatty liver, levels of produced lipids were measured and an effect of drug administration on reduction of lipids was predicted. The liver tissues were stained with an Oil red o working solution, to evaluate levels of produced lipids.

Blood was collected and centrifuged at 3000 rpm at 4° C. for 10 min. The serum of the upper layer was taken and the levels of alkaline phosphate (ALP), aspartate transminase (AST) and alanine transaminase (ALT) were measured using an automatic blood biochemical analyzer (AU480, Beckman 30-18 Coulter, USA) and the results were analyzed.

A ratio of liver weight to body weight was measured and the amount of triglyceride in liver tissues was measured to expect effects of drug administration on reduction of relative liver weight and triglyceride. The liver tissues were ground with a homogenizer, chloroform and methanol (2:1) were added thereto, the resulting mixture was centrifuged at 3,000 rpm and at 4° C. for 10 minutes and the organic solvent layer containing lipids was separated. The organic solvent in the separated lipid layer was removed in the dryer at 50° C. for 12 hours. The lipid-only tubes were immersed in 100% EtOH, and then suspended in a lipid-free tube and then assayed with a kit reagent for measuring triglyceride (AM157S-K, Asan, Korea).

FIG. 4 shows that, in a test using a fatty liver model animal induced by a high fat diet, a group, to which 3-phenyl-4-normalpropyl-1-(pyridin-2-yl)-1H-pyrazol-5-ol hydrochloride is administered as a drug in a daily single dose of 60 mg/kg, has effects of reducing relative liver weight and levels of ALT, ALP and AST in blood. As can be seen from FIG. 4A, the relative liver weight is significantly reduced in the drug-administered group, as compared to the vehicle group and the obeticholic acid administration group as the positive control group, after drug administration. FIGS. 4B, 4C and 4D show that levels of ALT, ALP and AST in blood are considerably decreased in the drug-administered group, as compared to the vehicle group and the obeticholic acid administration group, as the positive control group, after drug administration.

Example 3

Activity of 3-phenyl-4-normal-propyl-1-(pyridin-2-yl)-1H-pyrazol-5-ol hydrochloride on Inhibition of Fatty Liver [Test Using Fatty Liver Model Animal Induced by Diabetic db/db Mice]

As subject animals, 6-week-old male diabetic db/db mice (C57BLKS/J-leprdb/leprdb) were purchased from Jackson Laboratory (Bar Harbor, Me., USA). The mice were kept under standard conditions. When the mice became 8 weeks old after being bred for about 2 weeks, test substances were administered to the mice. For 12 weeks after the mice became 8 weeks old, test substances were separately administered to a vehicle administration group and a 3-phenyl-4-normalpropyl-1-(pyridin-2-yl)-1H-pyrazol-5-ol hydrochloride administration group.

A normal control group was used as a negative control.

After completion of the test, the animals were anesthetized, liver tissues were taken out from respective animals and blood for inspection was collected. The liver tissues were weighed and imaged. The liver tissues were immobilized in 10% buffered neutral formalin. The immobilized tissues were cut to a predetermined thickness, subjected to a general tissue treatment process, embedded in paraffin and produced into tissue sections with a size of 4 to 5 μm, and the tissue sections were subjected to Hematoxylin & Eosin (H&E stain) as a general staining method and were histopatho-logically observed.

In addition to H&E staining, Oil red-O staining was conducted in order to observe lipids induced by formation of fatty liver, levels of produced lipids were measured and an effect of drug administration on reduction of lipids was predicted. The liver tissues were stained with an Oil red 0 working solution, to evaluate levels of produced lipids.

Blood was collected and centrifuged at 3000 rpm at 4° C. for 10 min. The serum of the upper layer was taken and the levels of triglyceride (TG) and LDL-cholesterol (LDL-C) were measured using an automatic blood biochemical analyzer (AU480, Beckman 30-18 Coulter, USA) and the results were analyzed.

A ratio of liver weight to body weight was measured and the amount of triglyceride in liver tissues was measured to expect effects of drug administration on reduction of relative liver weight and triglyceride. The liver tissues were ground with a homogenizer, chloroform and methanol (2:1) were added thereto, the resulting mixture was centrifuged at 3,000 rpm and at 4° C. for 10 minutes and the organic solvent layer containing lipids was separated. The organic solvent in the separated lipid layer was removed in the dryer at 50° C. for 12 hours. The lipid-only tubes were immersed in 100% EtOH, and then suspended in a lipid-free tube and then assayed with a kit reagent for measuring triglyceride (AM157S-K, Asan, Korea).

Figure 5A:
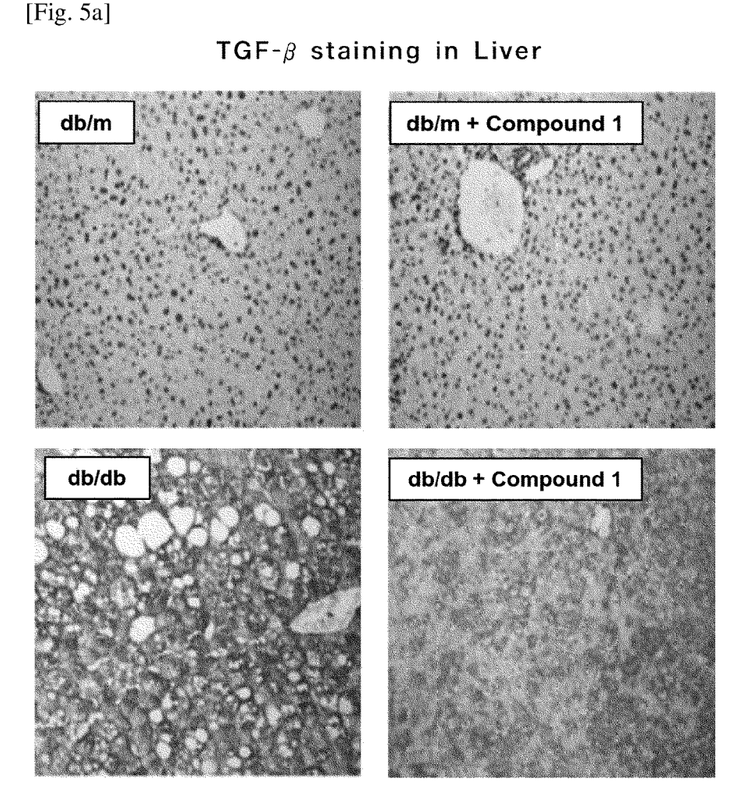
FIG. 5 is an image showing an effect of inhibition of hepatic fibrosis in the liver tissues in a test using a fatty liver model animal induced by a diabetic db/db mouse.
Figure 5B:
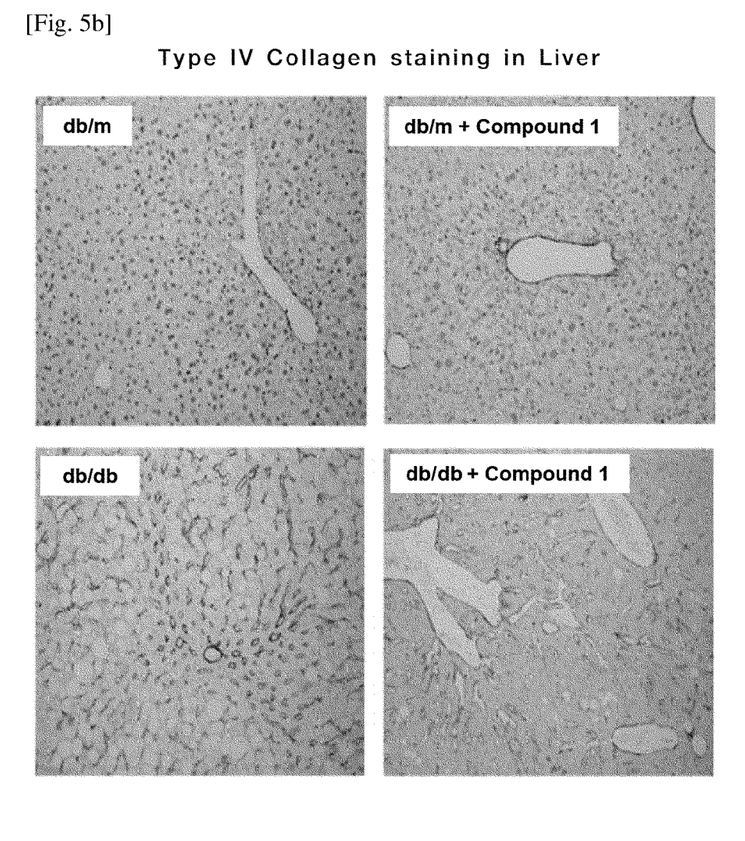
Figure 6A:
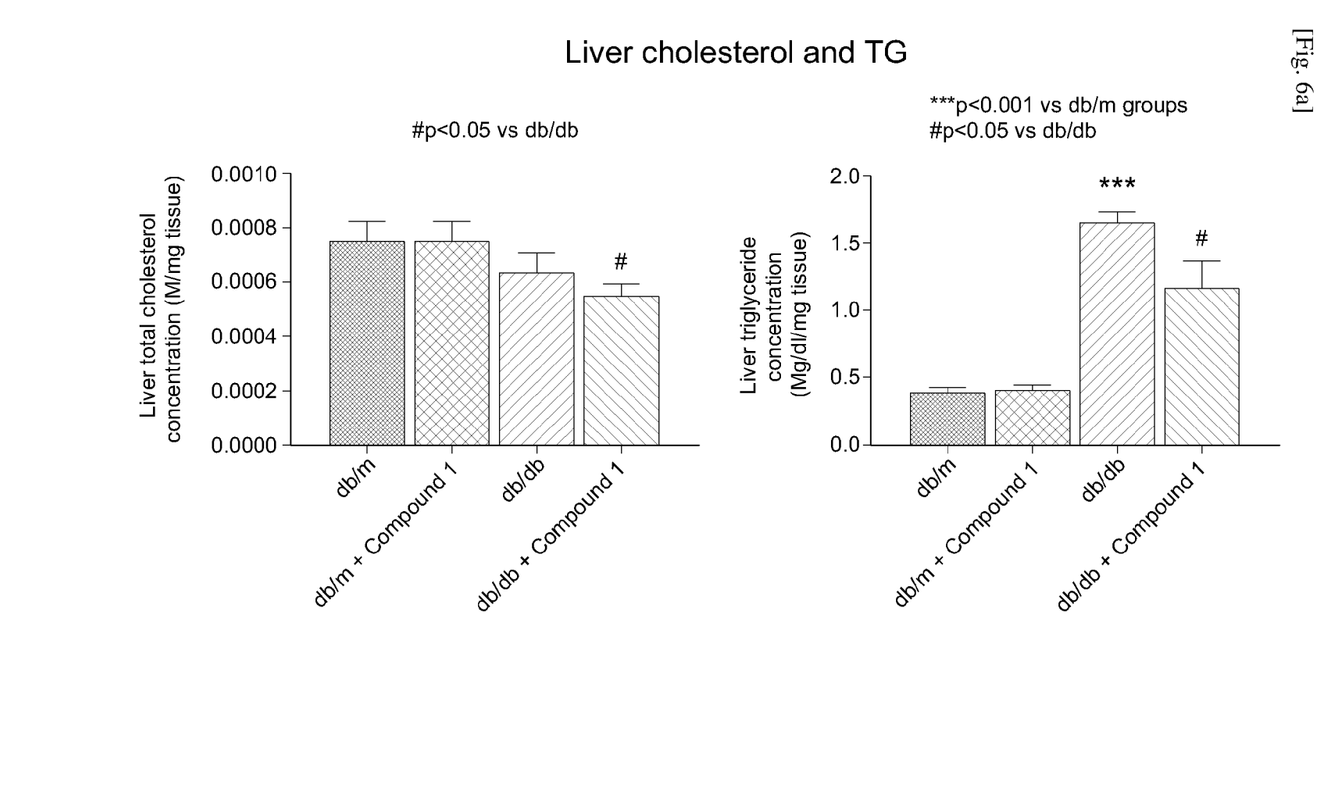
FIG. 6 shows effects of decreasing levels of TG and LDL in the liver tissues, inhibiting hepatic inflammation and hepatic fibrosis, and decreasing levels of TG and LDL in blood in a test using a fatty liver model animal induced by a diabetic db/db mouse.
Figure 6B:
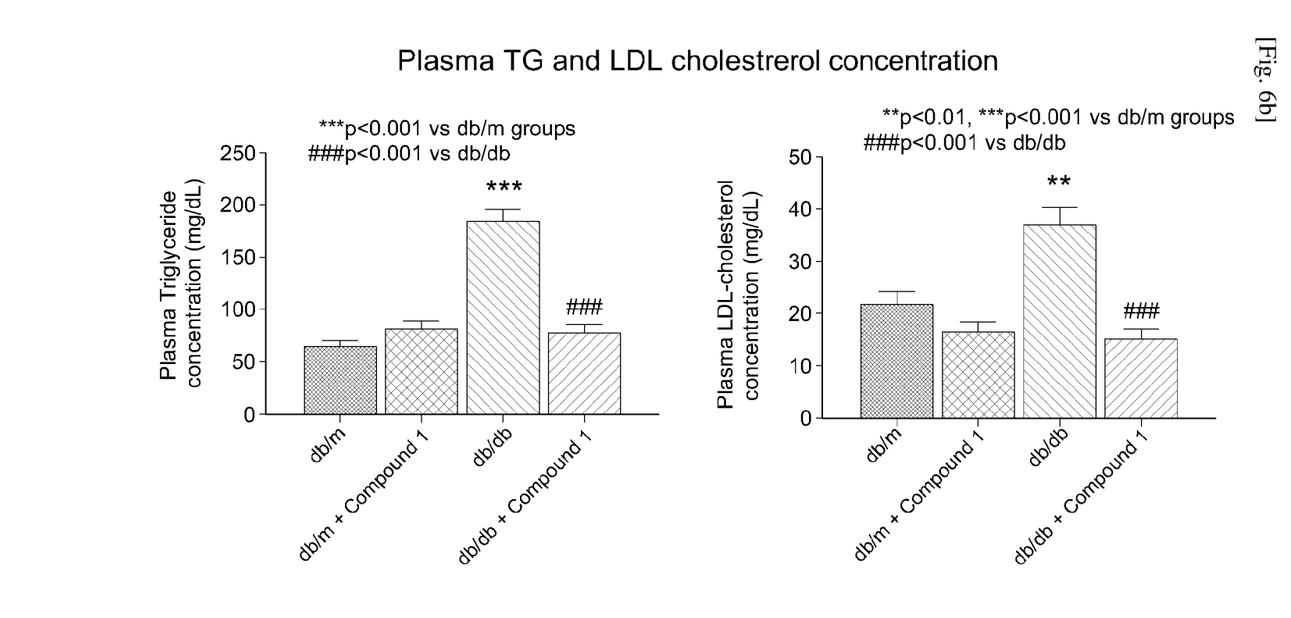
Figure 6C:
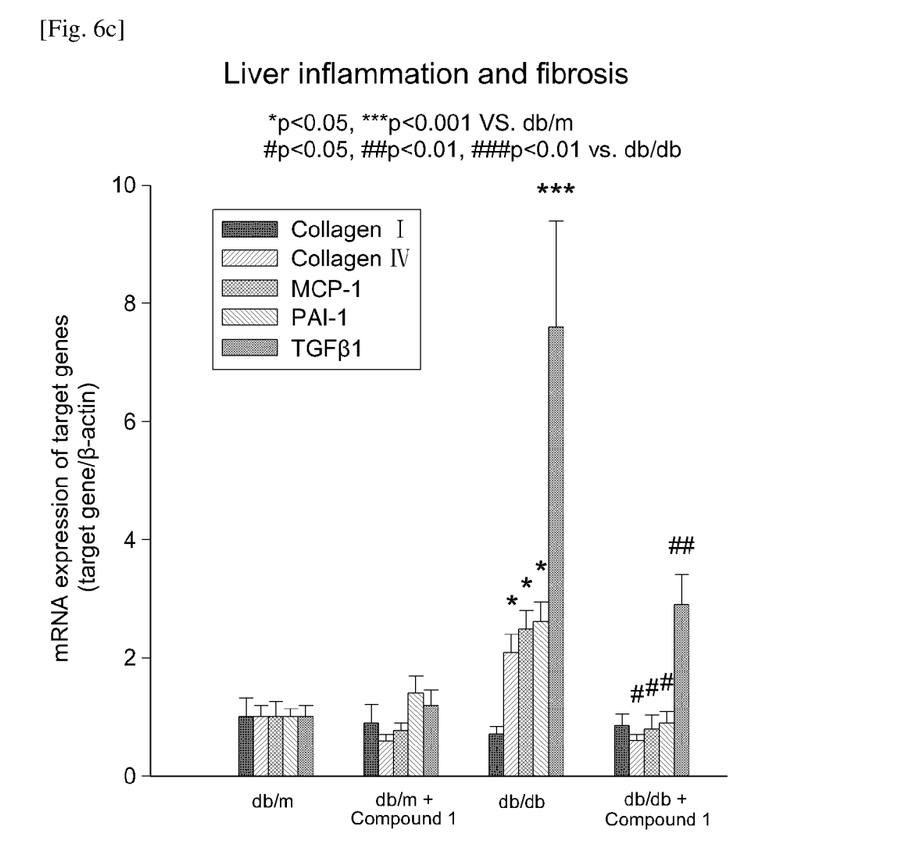

FIGS. 5 and 6 are images and graphs showing that, in a test using fatty liver model animals induced by diabetic db/db mice, a group, to which 3-phenyl-4-normalpropyl-1-(pyridin-2-yl)-1H-pyrazol-5-ol hydrochloride is administered as a drug in a daily single dose of 60 mg/kg, has effects of suppressing inflammation of liver tissues, inhibiting fibrosis of liver tissues, and decreasing levels of TG and LDL in blood and liver tissues. As can be seen from FIGS. 5 and 6, FIG. 5 shows results of TGF-β and Type IV collagen staining in liver tissues, to analyze liver tissues damage and hepatic fibrosis, which indicates that liver tissue damage and hepatic fibrosis are significantly reduced in the drug-administrated group, as compared to the vehicle group. FIGS. 6A and 6B show changes in TG and cholesterol in liver tissues and changes in TG and cholesterol in blood, which indicates that liver tissue damage and hepatic fibrosis are significantly reduced in the drug administration group, as compared to the vehicle group. FIG. 6C shows that mRNA expression of collagen I, collagen IV, MCP-1, PAI-1 and TGF-β, which are inflammation and fibrosis factors in liver tissues, are considerably reduced in the drug administration group, as compared to the vehicle group.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method for alleviating or treating a non-alcoholic fatty liver disease (NAFLD), the method comprising administering at least one compound selected from a pyrazole-based compound represented by the following Formula 1 and a pharmaceutically acceptable salt thereof:

[Formula 1]

wherein R is a C1-C10 linear or branched alkyl group.

2. The method according to claim 1, wherein the pyrazole-based compound is 3-phenyl-4-normalpropyl-1-(pyridin-2-yl)-1H-pyrazol-5-ol.

3. The method according to claim 1, wherein the pharmaceutically acceptable salt is selected from the group consisting of an alkali metal salt, an alkaline earth metal salt, a salt with an inorganic acid, a salt with an organic acid, and a salt with an acidic amino acid.

4. The method according to claim 1, wherein the pharmaceutically acceptable salt is hydrochloride.

5. The method according to claim 1, wherein the non-alcoholic fatty liver disease (NAFLD) comprises at least one of simple steatosis, non-alcoholic steatohepatitis (NASH) and cirrhosis.

6. The method according to claim 1, wherein the compound is administered in the form of a formulation selected from the group consisting of injections, granules, tablets, pills, capsules, gels, syrups, suspensions, emulsions, droplets and liquids.

7. A method for alleviating or treating hepatic inflammation, hepatic fibrosis, or cirrhosis in a subject having fatty liver disease, the method comprising administering at least one compound selected from a pyrazole-based compound represented by the following Formula 1 and a pharmaceutically acceptable salt thereof:

[Formula 1]

wherein R is a C1-C10 linear or branched alkyl group.

8. The method according to claim 7, wherein the pyrazole-based compound is 3-phenyl-4-normalpropyl-1-(pyridin-2-yl)-1H-pyrazol-5-ol.

9. The method according to claim 7, wherein the pharmaceutically acceptable salt is selected from the group consisting of an alkali metal salt, an alkaline earth metal salt, a salt with an inorganic acid, a salt with an organic acid, and a salt with an acidic amino acid.

10. The method according to claim 7, wherein the pharmaceutically acceptable salt is hydrochloride.

11. The method according to claim 7, wherein the compound is administered in the form of a formulation selected from the group consisting of injections, granules, tablets, pills, capsules, gels, syrups, suspensions, emulsions, droplets and liquids.

* * * * *